United States Patent
Ma et al.

(10) Patent No.: US 9,733,249 B2
(45) Date of Patent: Aug. 15, 2017

(54) MPL MUTATIONS IN JAK2 V617F NEGATIVE PATIENTS WITH MYELOPROLIFERATIVE DISEASE

(71) Applicant: Quest Diagnostics Investments Incorporated, Wilmington, DE (US)

(72) Inventors: Wanlong Ma, Aliso Viejo, CA (US); Maher Albitar, Coto De Caza, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 131 days.

(21) Appl. No.: 14/492,822

(22) Filed: Sep. 22, 2014

(65) Prior Publication Data

US 2015/0080255 A1    Mar. 19, 2015

Related U.S. Application Data

(62) Division of application No. 13/511,845, filed as application No. PCT/US2010/058781 on Dec. 2, 2010, now Pat. No. 8,841,074.

(60) Provisional application No. 61/266,971, filed on Dec. 4, 2009.

(51) Int. Cl.
*G01N 33/574* (2006.01)
*C12Q 1/68* (2006.01)

(52) U.S. Cl.
CPC ..... *G01N 33/57426* (2013.01); *C12Q 1/6883* (2013.01); *C12Q 2600/156* (2013.01); *G01N 2333/715* (2013.01)

(58) Field of Classification Search
None
See application file for complete search history.

(56) References Cited

U.S. PATENT DOCUMENTS

| | | |
|---|---|---|
| 2002/0177166 A1 | 11/2002 | Guthridge et al. |
| 2007/0042382 A1 | 2/2007 | Cargill et al. |

OTHER PUBLICATIONS

Kilpivaara et al, Leukemia 22:1813-1817 2008.*
International Search Report and Written Opinion mailed Mar. 11, 2011, in corresponding PCT/US2010/058781.
Kondo et al., "Familial Essential Thrombocythemia Associated With One-Base Deletion in the 5'Untranslated Region of the *Thrombopoietin* Gene," Blood, Aug. 15, 1998, 92(4):1091-1096.
Ma et al., "Mutation Profile of *JAK2* Transcripts in Patients with Chronic Myeloproliferative Neoplasias," Journal of Molecular Diagnostics, Jan. 2009, 11(1):49-53.
Ohashi et al., "Two rage MPL gene mutations in patients with essential thrombocythemia," Int. J. Hematol., vol. 90, pp. 431-432, 2009, published online Sep. 2, 2009.
Office Action issued in U.S. Appl. No. 13/511,845 on Feb. 27, 2013.
Office Action issued in U.S. Appl. No. 13/511,845 on Jul. 1, 2013.
Office Action issued in U.S. Appl. No. 13/511,845 on Dec. 31, 2013.
Notice of Allowance issued in U.S. Appl. No. 13/511,845 on Mar. 27, 2014.

* cited by examiner

*Primary Examiner* — Lei Yao
(74) *Attorney, Agent, or Firm* — Foley & Lardner LLP

(57) ABSTRACT

The invention provides compositions and methods for diagnosing a patient as having a myeloproliferative disease by identifying mutations in the MPL gene or gene products.

11 Claims, 8 Drawing Sheets

1618_1619 ag del/ins T, R525C fs*14

FIGURE 5A

```
   1 cctgaaggga ggatgggcta aggcaggcac acagtggcgg agaagatgcc ctcctgggcc
  61 ctcttcatgg tcacctcctg cctcctcctg gcccctcaaa acctggccca agtcagcagc
 121 caagatgtct ccttgctggc atcagactca gagcccctga agtgtttctc ccgaacattt
 181 gaggacctca cttgcttctg ggatgaggaa gaggcagcgc ccagtgggac ataccagctg
 241 ctgtatgcct acccgcggga gaagcccgt gcttgccccc tgagttccca gagcatgccc
 301 cactttggaa cccgatacgt gtgccagttt ccagaccagg aggaagtgcg tctcttcttt
 361 ccgctgcacc tctgggtgaa gaatgtgttc ctaaaccaga ctcggactca gcgagtcctc
 421 tttgtggaca gtgtaggcct gccggctccc cccagtatca tcaaggccat gggtgggagc
 481 cagccagggg aacttcagat cagctgggag gagccagctc cagaaatcag tgatttcctg
 541 aggtacgaac tccgctatgg ccccagagat cccaagaact ccactggtcc cacggtcata
 601 cagctgattg ccacagaaac ctgctgccct gctctgcaga ggcctcactc agcctctgct
 661 ctggaccagt ctccatgtgc tcagcccaca atgccctggc aagatggacc aaagcagacc
 721 tccccaagta gagaagcttc agctctgaca gcagagggtg gaagctgcct catctcagga
 781 ctccagcctg gcaactccta ctggctgcag ctgcgcagcg aacctgatgg gatctccctc
 841 ggtggctcct ggggatcctg gtccctccct gtgactgtgg acctgcctgg agatgcagtg
 901 gcacttggac tgcaatgctt taccttggac ctgaagaatg ttacctgtca atggcagcaa
 961 caggaccatg ctagctccca aggcttcttc taccacagca gggcacggtg ctgccccaga
1021 gacaggtacc ccatctggga gaactgcgaa gaggaagaga aaacaaatcc aggactacag
1081 accccacagt tctctcgctg ccacttcaag tcacgaaatg acagcattat tcacatcctt
1141 gtggaggtga ccacagcccc gggtactgtt cacagctacc tgggctcccc tttctggatc
1201 caccaggctg tgcgcctccc caccccaaac ttgcactgga gggagatctc cagtgggcat
1261 ctggaattgg agtggcagca cccatcgtcc tgggcagccc aagagacctg ttatcaactc
1321 cgatacacag gagaaggcca tcaggactgg aaggtgctgg agccgcctct cggggcccga
1381 ggagggaccc tggagctgcg cccgcgatct cgctaccgtt tacagctgcg cgccaggctc
1441 aacggcccca cctaccaagg tccctggagc tcgtggtcgg acccaactag ggtggagacc
1501 gccaccgaga ccgcctggat ctccttggtg accgctctgc atctagtgct gggcctcagc
1561 gccgtcctgg gcctgctgct gctgaggtgg cagtttcctg cacactacag gagactgagg
```

FIGURE 5B

```
1621 catgccctgt ggccctcact tccagacctg caccgggtcc taggccagta ccttagggac 1681 actgcagccc tgagcccgcc caaggccaca gtctcagata cctgtgaaga agtggaaccc 1741 agcctccttg aaatcctccc caagtcctca gagaggactc ctttgcccct gtgttcctcc 1801 caggcccaga tggactaccg aagattgcag ccttcttgcc tggggaccat gcccctgtct 1861 gtgtgcccac ccatggctga gtcagggtcc tgctgtacca cccacattgc caaccattcc 1921 tacctaccac taagctattg gcagcagcct tgaggacagg ctcctcactc ccagttccct 1981 ggacagagct aaactctcga gacttctctg tgaacttccc taccctaccc ccacaacaca 2041 agcaccccag acctcacctc catcccctc tgtctgccct cacaattagg cttcattgca 2101 ctgatcttac tctactgctg ctgacataaa accaggaccc tttctccaca ggcaggctca 2161 tttcactaag ctcctccttt actttctctc tcctctttga tgtcaaacgc cttgaaaaca 2221 agcctccact tccccacact tcccatttac tcttgagact acttcaatta gttcccctac 2281 tacactttgc tagtgaaact gcccaggcaa agtgcacctc aaatcttcta attccaagat 2341 ccaataggat ctcgttaatc atcagttcct ttgatctcgc tgtaagattt gtcaaggctg 2401 actactcact tctcctttaa attctttcct accttggtcc tgcctctttg agtatattag 2461 taggtttttt ttatttgttt gagacagggt ctcactctgt cacccaggct gcagtgcaat 2521 ggcgcgatct cagctcactg caacctccac ctccgggttc aagcgattct tgtgcctcgg 2581 cctccctagt agctgggatt acaggcgcac accaccacac acagctaatt ttttttttt 2641 ttttttttt tttttttag acggagcctt gctctgttgc cagactggag tgcagtggca 2701 cgatctcggc tcactgcaac ctctgcctcc cgggttcaag ccattctgcc tcagcctccc 2761 aagtagctgg gagtacaggc gtctgccacc atgcctaatt ttttctatt tttaggagag 2821 accggttttc accacgttgg ccaggatggt ctcgatatcc tgatctcgtg atccgcctgc 2881 ctctgcctcc caaagtgctg ggattacagg tgtgacccac tgcgcacagc cccagctaat 2941 tttcatattt ttagtagaga cagggttttg ccatgttgcc caggctggtc ttgaactcct 3001 aacctcgggt gatccaccca ccttggcctc ccaaagtgtt aggattacag gcatgagcca 3061 ctgcgcccgg ctgagtgtac tagtagttaa gagaataaac tagatctaga atcagagctg 3121 gattcaattc ctgtccttca catttactag ctgtgcaacc ttgggcacat aacttaatgt
```

FIGURE 5C

```
3181 ctttgagcct tagttttttc atctgtaaaa cagggataat aacagcaccc catagagttg 3241 tgacgaggat tgagataatc taagtaaagc acagtcccta ggacatagta aatgattcat 3301 atatccgaac tactgttata attattcctt cttactctcc tcttctagca tttcttccaa 3361 ttattacagt ccttcaagat tccatttctt aacagtctcc aatcccatct attctctgcc 3421 tttactatat gttgaccatt ccaaagttct tatctctagc tcagacatct actacagcac 3481 tgtgatgctt tatgcaacta actgtttaca tatctgtccc ctgctactag attgtgagct 3541 ccttgaggga aaggaacatg atttatttgt cctttttcccc cagcacctag agtagtgctt 3601 ggtgcatgat agtaggcctt caataaattt tttctaaatg aatga
```

FIGURE 6

```
MPSWALFMVT SCLLLAPQNL AQVSSQDVSL LASDSEPLKC FSRTFEDLTC FWDEEEAAPS
GTYQLLYAYP REKPRACPLS SQSMPHFGTR YVCQFPDQEE VRLFFPLHLW VKNVFLNQTR
TQRVLFVDSV GLPAPPSIIK AMGGSQPGEL QISWEEPAPE ISDFLRYELR YGPRDPKNST
GPTVIQLIAT ETCCPALQRP HSASALDQSP CAQPTMPWQD GPKQTSPSRE ASALTAEGGS
CLISGLQPGN SYWLQLRSEP DGISLGGSWG SWSLPVTVDL PGDAVALGLQ CFTLDLKNVT
CQWQQQDHAS SQGFFYHSRA RCCPRDRYPI WENCEEEEKT NPGLQTPQFS RCHFKSRNDS
IIHILVEVTT APGTVHSYLG SPFWIHQAVR LPTPNLHWRE ISSGHLELEW QHPSSWAAQE
TCYQLRYTGE GHQDWKVLEP PLGARGGTLE LRPRSRYRLQ LRARLNGPTY QGPWSSWSDP
TRVETATETA WISLVTALHL VLGLSAVLGL LLLRWQFPAH YRRLRHALWP SLPDLHRVLG
QYLRDTAALS PPKATVSDTC EEVEPSLLEI LPKSSERTPL PLCSSQAQMD YRRLQPSCLG
TMPLSVCPPM AESGSCCTTH IANHSYLPLS YWQQP
```

MPL MUTATIONS IN JAK2 V617F NEGATIVE PATIENTS WITH MYELOPROLIFERATIVE DISEASE

CROSS-REFERENCE TO RELATED APPLICATIONS

This application is a divisional of U.S. patent application Ser. No. 13/511,845, filed Aug. 31, 2012, which is a U.S. National Stage of PCT/US2010/058781, filed Dec. 2, 2010, which claims benefit of U.S. Provisional Application 61/266,971, filed Dec. 4, 2009, all of which are hereby incorporated by reference in their entirety.

FIELD OF THE INVENTION

This invention relates to the field of disease detection and more specifically to compositions and diagnostic methods useful for patients having hematopoietic disorders such as a myeloproliferative disease.

BACKGROUND OF THE INVENTION

The following description is provided to assist the understanding of the reader. Information provided or references cited herein neither constitute any admission nor limit claim scope.

Myeloproliferative diseases (MPD) are multipotent hematopoietic stem cell disorders characterized by excess production of various blood cells. MPNs include polycythemia vera (PV), essential thrombocythemia (ET), and idiopathic myelofibrosis (IMF). JAK2 V617F mutation is reported in about 95% of patients with PV, in 35% to 70% of patients with ET, and 50% of patients with IMF. Also, JAK2 exon 12 mutations are detected in some of the V617F-negative PV patients (Ma et al., J. Mol. Diagn., 11: 49-53, 2009) Furthermore, activating mutations in the thrombopoietin receptor gene (MPL) (e.g., W515L and W515K) have been reported in 5% and 1% in JAK2 V617F-negative patients with IMF and ET, respectively. (Pikman et al., PLoS Med., 3: 1140-1151, 2006)

JAK2 V617F is a gain-of-function mutation that leads to clonal proliferation; it is present in about 95% of PV cases and about 50% of ET and MF cases. The JAK2 allele burden decreases with successful therapy, disappears in some patients, and reappears during relapse. Thus, quantitative JAK2 analysis may be useful for diagnosis and patient management.

Although JAK2 V617F mutations can be identified in many patients with PV, ET and MF, a significant proportion of patients with ET and MF and a small number of patients with PV are JAK2 V617F negative. Clonal hematopoiesis is observed in patients with JAK2 V617F-negative MPD, suggesting alternate alleles account for myeloproliferation in this setting. (Levine et al. Blood 107: 4039-4041, 2006). Moreover, serial assessment of JAK2 V617F status in JAK2 V617F-negative MPD did not observe conversion to JAK2 V617F-positive MPD, indicating JAK2 V617F-negative MPD are pathogenetically distinct from JAK2 V617F-positive MPD. (Campbell et al. Blood 108: 3548-3555, 2006).

SUMMARY OF THE INVENTION

The present inventions are based on the discovery of mutations in the MPL gene including insertion/deletion mutations and point mutations in patients diagnosed or suspected to have a myeloproliferative disease. These mutations result in mutated and truncated MPL proteins.

In one aspect, the invention provides a method for diagnosing a myeloproliferative disease in an individual by: a) evaluating a sample containing nucleic acids from the individual for the presence or absence of one or more mutations in MPL nucleic acid including the T1588_T1599 del/ins 6, C1533_G1534 ins 12, and A1618_G1619 del/ins T mutations; and b) identifying the individual as having a hematopoietic disease when the MPL nucleic acid comprises at least one mutation. The sample may be any suitable biological sample including, for example, whole blood (i.e., MPL nucleic acid being extracted from the cellular fraction), plasma, serum, and tissue samples (e.g., biopsy and paraffin-embedded tissue). The MPL nucleic acid may be any convenient nucleic acid type including, for example, genomic DNA, RNA (e.g., mRNA), or cDNA prepared from subject RNA. Alternatively, the MPL nucleic acid mutation may be inferred by assessing the MPL protein from the individual. For example, identification of a mutant MPL protein is indicative of a mutation in the MPL gene. Suitable detection methodologies include oligonucleotide probe hybridization, primer extension reaction, nucleic acid sequencing, and protein sequencing. In some embodiments, the individual is screened for the presence of a pathological JAK2 mutation either simultaneously or prior to screening for the MPL nucleic acid mutation. In some embodiments, individuals are first identified as lacking a pathological JAK2 mutation (e.g, the V617F mutation) and subsequently screened for an MPL nucleic acid mutation.

The invention also provided oligonucleotides (e.g., primers and probes) suitable for assessing MPL nucleic acid mutations. For example, suitable probes are designed to specifically hybridize to a nucleotide sequence containing at least one MPL mutation disclosed herein (i.e., but not hybridize to a non-mutated sequence). Suitable primers include allele-specific primers and primers suitable for primer extension reactions (e.g., SNaPShot® primers). The invention also provides antibodies that specifically bind to mutated MPL proteins encoded by the mutated MPL nucleic acids disclosed herein.

The invention also provides a method of assessing the myeloproliferative disease status of an individual, comprising: (a) evaluating a sample containing nucleic acids from the individual for the presence or absence of one or more mutations in both alleles of the MPL gene, said nucleic acid mutations being selected from the group consisting of the T1588_T1599 del/ins 6, C1533_G1534 ins 12, and A1618_G1619 del/ins T mutations; and (b) identifying the individual (i) as having a myeloproliferative disease or being predisposed to myeloproliferative disease when the individual is homozygous for one of said mutations (ii) as being predisposed to a myeloproliferative disease when the individual is heterozygous for one of said mutations, or (iii) as having no predisposition to a myeloproliferative disease caused by one of said mutations when each of said mutations is absent from both alleles of the MPL gene.

In one embodiment, the nucleic acid from the individual is RNA. In a further embodiment, evaluating comprises amplifying MPL nucleic acid and performing sequencing analysis of the amplified nucleic acid.

In another aspect, the invention provides a method of assessing the myeloproliferative disease status of an individual, comprising: (a) evaluating a sample containing MPL protein from the individual for the presence or absence of one or more MPL protein mutations and wild type MPL protein, said protein mutations being selected from the group consisting of the W515_P518 del/insKT, the T496_A497 insATVI, and the R525C fs*14 mutations; and (b) identifying the individual (i) as having a myeloproliferative disease or being predisposed to myeloproliferative disease when the sample shows the presence of one or more of said protein mutations and the absence wild type MPL protein, (ii) as being predisposed to a myeloproliferative disease when the individual shows the presence of wild type MPL protein and one or more of said protein mutations, or (iii) as having no predisposition to a myeloproliferative disease when the individual shows the absence of each of said protein mutations.

In one embodiment of the foregoing aspect, evaluating comprises using antibodies against wild type MPL protein and each of the protein mutations. In another embodiment, evaluating comprises using protein sequencing.

In yet another aspect, the invention provides a method of identifying an individual with an increased likelihood of having a myeloproliferative disease, comprising: (a) evaluating a sample containing nucleic acids from the individual for the presence or absence of one or more mutations in both alleles of the MPL gene, said nucleic acid mutations being selected from the group consisting of the T1588_T1599 del/ins 6, C1533_G1534 ins 12, and A1618_G1619 del/ins T mutations; and (b) identifying the individual as having an increased likelihood of having a myeloproliferative disease when one of said mutations is present in at least one allele.

In one embodiment of the foregoing aspect, the nucleic acid from the individual is RNA. In a further embodiment, evaluating comprises sequencing the MPL nucleic acid.

In still another aspect, the invention provides a method of identifying an individual with an increased likelihood of having a myeloproliferative disease, comprising: (a) evaluating a sample containing protein from the individual for the presence or absence of one or more MPL protein mutations, said protein mutations being selected from the group consisting of the W515_P518 del/insKT, T496_A497 insATVI, and R525C fs*14 mutations; and (b) identifying the individual as having an increased likelihood of having a myeloproliferative disease when one of said mutations is present.

In one embodiment of the foregoing aspect, evaluating comprises using antibodies against wild type MPL protein and each of the protein mutations. In another embodiment, evaluating comprises using protein sequencing.

In an embodiment of any of the foregoing aspects, the sample is selected from the group consisting of blood, serum, and plasma. In another embodiment, myeloproliferative disease is selected from the group consisting of polycythemia vera (PV), essential thrombocythemia (ET), and idiopathic myelofibrosis (IMF).

In another embodiment of any of the foregoing aspects, evaluating comprises amplifying MPL nucleic acid and hybridizing the amplified nucleic acid with a detection oligonucleotide that is capable of specifically detecting JAK2 nucleic acid under hybridization conditions. Another embodiment further comprises said individual not having a pathologic mutation in the JAK2 gene. Another embodiment further comprises said individual not having a mutation in the JAK2 gene encoding V617F mutation.

The term "T1588_T1599 del/ins 6 mutation" refers to a mutation in the MPL gene in which the nucleotides corresponding to nucleotides 1588-1599 of SEQ ID NO: 1 are deleted (i.e., tgg cag ttt cct; SEQ ID NO: 8) and the hexanucleotide -aaa act- (SEQ ID NO: 9) is inserted in its place. This in-frame insertion/deletion (indel) mutation results in the W515_P518 del/insKT mutation in the MPL protein in which the tetrapeptide -WQFP- at amino acid positions 515-518 of SEQ ID NO: 2 is deleted and replaced by a lysine-threonine dipeptide.

The term "C1533_G1534 ins 12 mutation" refers to a mutation in the MPL gene in which a 12 nucleotide insert having the sequence -gct ctg gtg atc- (SEQ ID NO: 7) is inserted between nucleotides 1533 and 1534 of SEQ ID NO: 1. This in-frame insertion mutation results in the T496_A497 insATVI mutation in the MPL protein in which the tetrapeptide -ATVI- is inserted between amino acids 496 and 497 of SEQ ID NO: 2.

The term "A1618_G1619 del/ins T mutation" refers to a mutation in the MPL gene in which the nucleotides at position 1618-1619 of SEQ ID NO: 1 are deleted and replaced with a single thymine. This frame shift mutation results in the R525C fs*14 mutation in the MPL protein, in which the resulting mutated MPL protein has a C-terminus comprising 14 non-native amino acids at amino acids 525-538 relative to SEQ ID NO: 2 and a pre-mature stop codon which truncates further protein translation. The mutated MPL protein has the following C-terminus: -CMPCGPHFQTCTGS (SEQ ID NO: 15).

The term "zygosity status" as used herein means whether an individual is homozygous for a gene or gene mutation, i.e. both alleles have the same copy of a gene or gene mutation, or heterozygous for a gene or gene mutation, i.e. only one allele has a copy of the gene or gene mutation.

The term "myeloproliferative disease" as used herein means a disorder of a bone marrow or lymph node-derived cell type, such as a white blood cell. A myeloproliferative disease is generally manifest by abnormal cell division resulting in an abnormal level of a particular hematological cell population. The abnormal cell division underlying a proliferative hematological disorder is typically inherent in the cells and not a normal physiological response to infection or inflammation. Leukemia is a type of myeloproliferative disease. Exemplary myeloproliferative diseases include, but are not limited to, acute myeloid leukemia (AML), acute lymphoblastic leukemia (ALL), chronic lymphocytic leukemia (CLL), myelodysplastic syndrome (MDS), chronic myeloid leukemia (CML), hairy cell leukemia, leukemic manifestations of lymphomas, multiple myeloma, polycythemia vera (PV), essential thrombocythemia (ET), idiopathic myelofibrosis (IMF), hypereosinophilic syndrome (HES), chronic neutrophilic leukemia (CNL), myelofibrosis with myeloid metaplasia (MMM), chronic myelomonocytic leukemia (CMML), juvenile myelomonocytic leukemia, chronic basophilic leukemia, chronic eosinophilic leukemia, systemic mastocytosis (SM), and unclassified myeloproliferative diseases (UMPD or MPD-NC). Lymphoma is a type of proliferative disease that mainly involves lymphoid organs, such as lymph nodes, liver, and spleen. Exemplary proliferative lymphoid disorders include lymphocytic lymphoma (also called chronic lymphocytic leukemia), follicular lymphoma, large cell lymphoma, Burkitt's lymphoma, marginal zone lymphoma, lymphoblastic lymphoma (also called acute lymphoblastic lymphoma).

The term "diagnose" or "diagnosis" or "diagnosing" as used herein refer to distinguishing or identifying a disease, syndrome or condition or distinguishing or identifying a person having a particular disease, syndrome or condition. Usually, a diagnosis of a disease or disorder is based on the evaluation of one or more factors and/or symptoms that are indicative of the disease. That is, a diagnosis can be made based on the presence, absence or amount of a factor which is indicative of presence or absence of the disease or condition. Each factor or symptom that is considered to be indicative for the diagnosis of a particular disease does not need be exclusively related to the particular disease; i.e. there may be differential diagnoses that can be inferred from a diagnostic factor or symptom. Likewise, there may be instances where a factor or symptom that is indicative of a particular disease is present in an individual that does not have the particular disease.

The term "prognosis" as used herein refers to a prediction of the probable course and outcome of a clinical condition or disease. A prognosis of a patient is usually made by evaluating factors or symptoms of a disease that are indicative of a favorable or unfavorable course or outcome of the disease.

The phrase "determining the prognosis" as used herein refers to the process by which the skilled artisan can predict the course or outcome of a condition in a patient. The term "prognosis" does not refer to the ability to predict the course or outcome of a condition with 100% accuracy. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition. A prognosis may be expressed as the amount of time a patient can be expected to survive. Alternatively, a prognosis may refer to the likelihood that the disease goes into remission or to the amount of time the disease can be expected to remain in remission. Prognosis can be expressed in various ways; for example prognosis can be expressed as a percent chance that a patient will survive after one year, five years, ten years or the like. Alternatively prognosis may be expressed as the number of years, on average that a patient can expect to survive as a result of a condition or disease. The prognosis of a patient may be considered as an expression of relativism, with many factors effecting the ultimate outcome. For example, for patients with certain conditions, prognosis can be appropriately expressed as the likelihood that a condition may be treatable or curable, or the likelihood that a disease will go into remission, whereas for patients with more severe conditions prognosis may be more appropriately expressed as likelihood of survival for a specified period of time.

The term "poor prognosis" as used herein, in the context of a patient having a leukemia and a mutation in the MPL gene, refers to an increased likelihood that the patient will have a worse outcome in a clinical condition relative to a patient diagnosed as having the same disease but without the mutation. A poor prognosis may be expressed in any relevant prognostic terms and may include, for example, the expectation of a reduced duration of remission, reduced survival rate, and reduced survival duration.

As used herein, the term "sample" or "biological sample" refers to any liquid or solid material obtained from a biological source, such a cell or tissue sample or bodily fluids. "Bodily fluids" include, but are not limited to, blood, serum, plasma, saliva, cerebrospinal fluid, pleural fluid, tears, lactal duct fluid, lymph, sputum, urine, saliva, amniotic fluid, and semen. A sample may include a bodily fluid that is "acellular." An "acellular bodily fluid" includes less than about 1% (w/w) whole cellular material. Plasma or serum are examples of acellular bodily fluids. A sample may include a specimen of natural or synthetic origin. Exemplary sample tissues include, but are not limited to bone marrow or tissue (e.g. biopsy material).

As used herein, the term "specifically binds," when referring to a binding moiety, is meant that the moiety is capable of discriminating between a various target sequences. For example, an oligonucleotide (e.g., a primer or probe) that specifically binds to a mutant target sequence is one that hybridizes preferentially to the target sequence (e.g., the wildtype sequence) over the other sequence variants (e.g., mutant and polymorphic sequences). Preferably, oligonucleotides specifically bind to their target sequences under high stringency hybridization conditions.

As used herein the term "stringency" is used in reference to the conditions of temperature, ionic strength, and the presence of other compounds, under which nucleic acid hybridizations are conducted. With high stringency conditions, nucleic acid base pairing will occur only between nucleic acids that have sufficiently long segment with a high frequency of complementary base sequences.

Exemplary hybridization conditions are as follows. High stringency generally refers to conditions that permit hybridization of only those nucleic acid sequences that form stable hybrids in 0.018M NaCl at 65° C. High stringency conditions can be provided, for example, by hybridization in 50% formamide, 5×Denhardt's solution, 5×SSC (saline sodium citrate) 0.2% SDS (sodium dodecyl sulphate) at 42° C., followed by washing in 0.1×SSC, and 0.1% SDS at 65° C. Moderate stringency refers to conditions equivalent to hybridization in 50% formamide, 5×Denhardt's solution, 5×SSC, 0.2% SDS at 42° C., followed by washing in 0.2×SSC, 0.2% SDS, at 65° C. Low stringency refers to conditions equivalent to hybridization in 10% formamide, 5×Denhardt's solution, 6×SSC, 0.2% SDS, followed by washing in 1×SSC, 0.2% SDS, at 50° C.

BRIEF DESCRIPTION OF THE DRAWINGS

FIG. 5A to FIG. 5C are the nucleotide sequence of the MPL cDNA provided in Genbank accession no. NM_005373.2 (SEQ ID NO: 1).

FIG. 6 is the amino acid sequence of the MPL protein encoded by the MPL cDNA of FIG. 5A to FIG. 5C (SEQ ID NO: 2).

DETAILED DESCRIPTION

Figure 1:
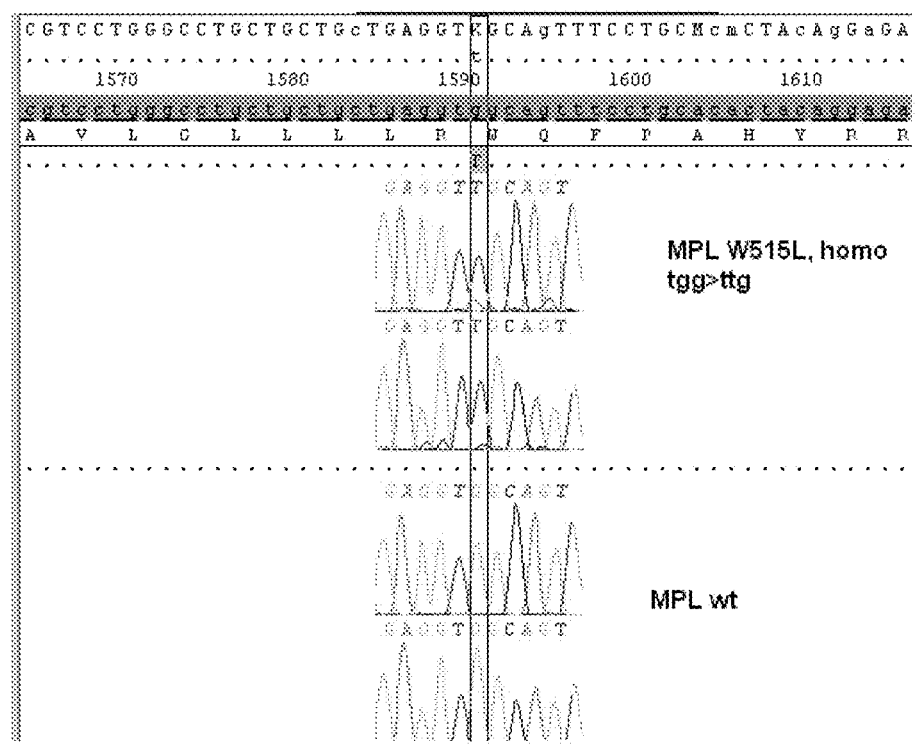
FIG. 1. is a representative sequence tracing showing a homozygous MPL W515L mutation.

The present invention is based on the identification of several mutations in exons 10 and 11 of the MPL gene in patients diagnosed with leukemia. The mutations include the T1588_T1599 del/ins 6 mutation, the C1533_G1534 ins 12 mutation, and the A1618_G1619 del/ins T mutation. Accordingly, the invention also provides variant nucleic acids with these gene mutations and the resulting mutated proteins, methods and reagents for the detection of the variants disclosed herein, uses of these variants for the development of detection reagents, and assays or kits that utilize such reagents.

T1588_T1599 del/ins 6 Mutation

The T1588_T1599 del/ins 6 mutation in the MPL gene may be assessed by any suitable method including, for example, by nucleic acid sequencing or oligonucleotide hybridization. For example, the T1588_T1599 del/ins 6 mutation may be assessed by amplifying a target sequence of an MPL nucleic acid (e.g., genomic DNA, RNA, or cDNA) containing all or a portion of the mutation. Relatedly, detection may involve using probes and/or primers capable of specifically hybridizing to the mutation site. One suitable target nucleic acid sequence from the MPL gene for assessing the presence of this mutation comprises the sequence: --ggaaaactgc-- (SEQ ID NO: 10). Target sequences (including primer and probe sequences encompassing this mutation) may be of any suitable length (e.g., 20, 25, 30, 35, 40, 50, 100, 200, 300, or more nucleotides in length).

Alternatively, the presence of the T1588_T1599 del/ins 6 mutation may be assessed by evaluating the MPL protein present in a patient sample such as by specifically detecting the W515_P518 del/insKT MPL protein variant. MPL protein assessment may be performed by any appropriate method including amino acid sequencing or through the use of mutant MPL-specific antibodies (e.g., using an ELISA). Mutant MPL proteins may be assessed by amino acid sequencing of all or a portion of the MPL protein comprising the amino acid sequence -LLLRKTAH- (SEQ ID NO: 11). Optionally, antibodies (polyclonal or monoclonal) can by raised against the a polypeptide epitope having the sequence of SEQ ID NO: 11.

C1533_G1534 ins 12 Mutation

The C1533_G1534 ins 12 mutation in the MPL gene may be assessed by any suitable method including, for example, by nucleic acid sequencing or oligonucleotide hybridization. For example, the C1533_G1534 ins 12 mutation may be assessed by amplifying a target sequence of an MPL nucleic acid (e.g., genomic DNA, RNA, or cDNA) containing all or a portion of the mutation. Relatedly, detection may involve using probes and/or primers capable of specifically hybridizing to the mutation site. One suitable target nucleic acid sequence from the MPL gene for assessing the presence of this mutation comprises the sequence: --ccgctctggtgatcgc-- (SEQ ID NO: 12). Target sequences (including primer and probe sequences encompassing this mutation) may be of any suitable length (e.g., 20, 25, 30, 35, 40, 50, 100, 200, 300, or more nucleotides in length).

Alternatively, the presence of the C1533_G1534 ins 12 mutation may be assessed by evaluating the MPL protein present in a patient sample such as by specifically detecting the T496_A497 insATVI MPL protein variant. MPL protein assessment may be performed by any appropriate method including amino acid sequencing or through the use of mutant MPL-specific antibodies (e.g., using an ELISA). Mutant MPL proteins may be assessed by amino acid sequencing of all or a portion of the MPL protein comprising the amino acid sequence -VTATVIAL- (SEQ ID NO: 13). Optionally, antibodies (polyclonal or monoclonal) can by raised against the a polypeptide epitope having the sequence of SEQ ID NO: 13.

A1618_G1619 del/insT Mutation

The A1618_G1619 del/ins T mutation in the MPL gene may be assessed by any suitable method including, for example, by nucleic acid sequencing or oligonucleotide hybridization. For example, the A1618_G1619 del/ins T mutation may be assessed by amplifying a target sequence of an MPL nucleic acid (e.g., genomic DNA, RNA, or cDNA) containing all or a portion of the mutation. Relatedly, detection may involve using probes and/or primers capable of specifically hybridizing to the mutation site. One suitable target nucleic acid sequence from the MPL gene for assessing the presence of this mutation comprises the sequence: --gactgtgcatg-- (SEQ ID NO: 14).

Alternatively, the presence of the A1618_G1619 del/ins T mutation may be assessed by evaluating the MPL protein present in a patient sample such as by specifically detecting the R525C fs*14 MPL protein variant. MPL protein assessment may be performed by any appropriate method including amino acid sequencing or through the use of mutant MPL-specific antibodies (e.g., using an ELISA). Mutant MPL proteins may be assessed by amino acid sequencing of all or the C-terminal portion of the MPL protein or using antibodies (polyclonal or monoclonal) raised against the mutated C-terminus.

Sample Collection and Preparation

The methods and compositions of this invention may be used to detect mutations in the MPL gene using a biological sample obtained from an individual. The nucleic acid (DNA or RNA) may be isolated from the sample according to any methods well known to those of skill in the art. Examples include tissue samples or any cell-containing or acellular bodily fluid. Biological samples may be obtained by standard procedures and may be used immediately or stored, under conditions appropriate for the type of biological sample, for later use.

Methods of obtaining test samples are well known to those of skill in the art and include, but are not limited to, aspirations, tissue sections, drawing of blood or other fluids, surgical or needle biopsies, and the like. The test sample may be obtained from an individual or patient diagnosed as having a myeloproliferative disorder or suspected being afflicted with a myeloproliferative disorder. The test sample may be a cell-containing liquid or a tissue. Samples may include, but are not limited to, amniotic fluid, biopsies, blood, blood cells, bone marrow, fine needle biopsy samples, peritoneal fluid, amniotic fluid, plasma, pleural fluid, saliva, semen, serum, tissue or tissue homogenates, frozen or paraffin sections of tissue. Samples may also be processed, such as sectioning of tissues, fractionation, purification, or cellular organelle separation.

If necessary, the sample may be collected or concentrated by centrifugation and the like. The cells of the sample may be subjected to lysis, such as by treatments with enzymes, heat, surfactants, ultrasonication, or a combination thereof. The lysis treatment is performed in order to obtain a sufficient amount of nucleic acid derived from the individual's cells to detect using polymerase chain reaction.

Methods of plasma and serum preparation are well known in the art. Either "fresh" blood plasma or serum, or frozen (stored) and subsequently thawed plasma or serum may be used. Frozen (stored) plasma or serum should optimally be maintained at storage conditions of −20 to −70° C. until thawed and used. "Fresh" plasma or serum should be refrigerated or maintained on ice until used, with nucleic acid (e.g., RNA, DNA or total nucleic acid) extraction being performed as soon as possible. Exemplary methods are described below.

Blood can be drawn by standard methods into a collection tube, typically siliconized glass, either without anticoagulant for preparation of serum, or with EDTA, sodium citrate, heparin, or similar anticoagulants for preparation of plasma. If preparing plasma or serum for storage, although not an absolute requirement, is that plasma or serum is first fractionated from whole blood prior to being frozen. This reduces the burden of extraneous intracellular RNA released from lysis of frozen and thawed cells which might reduce the sensitivity of the amplification assay or interfere with the amplification assay through release of inhibitors to PCR such as porphyrins and hematin. "Fresh" plasma or serum may be fractionated from whole blood by centrifugation, using gentle centrifugation at 300-800 times gravity for five to ten minutes, or fractionated by other standard methods. High centrifugation rates capable of fractionating out apoptotic bodies should be avoided. Since heparin may interfere with RT-PCR, use of heparinized blood may require pretreatment with heparanase, followed by removal of calcium prior to reverse transcription. Imai, H., et al., J. Virol. Methods 36:181-184, (1992). Thus, EDTA is a suitable anticoagulant for blood specimens in which PCR amplification is planned.

Nucleic Acid Extraction and Amplification

The nucleic acid to be amplified may be from a biological sample such as an organism, cell culture, tissue sample, and the like. The biological sample can be from a subject which includes any animal, preferably a mammal. A preferred subject is a human, which may be a patient presenting to a medical provider for diagnosis or treatment of a disease. The volume of plasma or serum used in the extraction may be varied dependent upon clinical intent, but volumes of 100 µL to one milliliter of plasma or serum are usually sufficient.

Various methods of extraction are suitable for isolating the DNA or RNA. Suitable methods include phenol and chloroform extraction. See Maniatis et al., Molecular Cloning, A Laboratory Manual, 2d, Cold Spring Harbor Laboratory Press, page 16.54 (1989). Numerous commercial kits also yield suitable DNA and RNA including, but not limited to, QIAamp™ mini blood kit, Agencourt Genfind™, Roche Cobas® Roche MagNA Pure® or phenol:chloroform extraction using Eppendorf Phase Lock Gels®, and the NucliSens extraction kit (Biomerieux, Marcy l'Etoile, France). In other methods, mRNA may be extracted from patient blood/bone marrow samples using MagNA Pure LC mRNA HS kit and Mag NA Pure LC Instrument (Roche Diagnostics Corporation, Roche Applied Science, Indianapolis, Ind.).

Nucleic acid extracted from tissues, cells, plasma or serum can be amplified using nucleic acid amplification techniques well know in the art. Many of these amplification methods can also be used to detect the presence of mutations simply by designing oligonucleotide primers or probes to interact with or hybridize to a particular target sequence in a specific manner. By way of example, but not by way of limitation, these techniques can include the polymerase chain reaction (PCR), reverse transcriptase polymerase chain reaction (RT-PCR), nested PCR, ligase chain reaction. See Abravaya, K., et al., Nucleic Acids Research, 23:675-682, (1995), branched DNA signal amplification, Urdea, M. S., et al., AIDS, 7 (suppl 2):S11-S 14, (1993), amplifiable RNA reporters, Q-beta replication, transcription-based amplification, boomerang DNA amplification, strand displacement activation, cycling probe technology, isothermal nucleic acid sequence based amplification (NASBA). See Kievits, T. et al., J Virological Methods, 35:273-286, (1991), Invader Technology, or other sequence replication assays or signal amplification assays. These methods of amplification each described briefly below and are well-known in the art.

Some methods employ reverse transcription of RNA to cDNA. As noted, the method of reverse transcription and amplification may be performed by previously published or recommended procedures, which referenced publications are incorporated herein by reference in their entirety. Various reverse transcriptases may be used, including, but not limited to, MMLV RT, RNasc H mutants of MMLV RT such as Superscript and Superscript II (Life Technologies, GIBCO BRL, Gaithersburg, Md.), AMV RT, and thermostable reverse transcriptase from *Thermus Thermophilus*. For example, one method, but not the only method, which may be used to convert RNA extracted from plasma or serum to cDNA is the protocol adapted from the Superscript II Preamplification system (Life Technologies, GIBCO BRL, Gaithersburg, Md.; catalog no. 18089-011), as described by Rashtchian, A., PCR Methods Applic., 4:S83-S91, (1994).

PCR is a technique for making many copies of a specific template DNA sequence. The reaction consists of multiple amplification cycles and is initiated using a pair of primer sequences that hybridize to the 5' and 3' ends of the sequence to be copied. The amplification cycle includes an initial denaturation, and typically up to 50 cycles of annealing, strand elongation and strand separation (denaturation). In each cycle of the reaction, the DNA sequence between the primers is copied. Primers can bind to the copied DNA as well as the original template sequence, so the total number of copies increases exponentially with time. PCR can be performed as according to Whelan, et al., J of Clin Micro, 33(3):556-561(1995). Briefly, a PCR reaction mixture includes two specific primers, dNTPs, approximately 0.25 U of Taq polymerase, and 1×PCR Buffer.

LCR is a method of DNA amplification similar to PCR, except that it uses four primers instead of two and uses the enzyme ligase to ligate or join two segments of DNA. LCR can be performed as according to Moore et al., J Clin Micro, 36(4):1028-1031 (1998). Briefly, an LCR reaction mixture contains two pair of primers, dNTP, DNA ligase and DNA polymerase representing about 90 µl, to which is added 100 µl of isolated nucleic acid from the target organism. Amplification is performed in a thermal cycler (e.g., LCx of Abbott Labs, Chicago, Ill.).

TAS is a system of nucleic acid amplification in which each cycle is comprised of a cDNA synthesis step and an RNA transcription step. In the cDNA synthesis step, a sequence recognized by a DNA-dependent RNA polymerase (i.e., a polymerase-binding sequence or PBS) is inserted into the cDNA copy downstream of the target or marker sequence to be amplified using a two-domain oligonucleotide primer. In the second step, an RNA polymerase is used to synthesize multiple copies of RNA from the cDNA template. Amplification using TAS requires only a few cycles because DNA-dependent RNA transcription can result in 10-1000 copies for each copy of cDNA template. TAS can be performed according to Kwoh et al., PNAS, 86:1173-7 (1989). Briefly, extracted RNA is combined with TAS amplification buffer and bovine serum albumin, dNTPs, NTPs, and two oligonucleotide primers, one of which contains a PBS. The sample is heated to denature the RNA template and cooled to the primer annealing temperature. Reverse transcriptase (RT) is added the sample incubated at the appropriate temperature to allow cDNA elongation. Subsequently T7 RNA polymerase is added and the sample is incubated at 37° C. for approximately 25 minutes for the synthesis of RNA. The above steps are then repeated. Alternatively, after the initial cDNA synthesis, both RT and RNA polymerase are added following a 1 minute 100° C. denaturation followed by an RNA elongation of approximately 30 minutes at 37° C. TAS can be also be performed on solid phase as according to Wylie et al., J Clin Micro, 36(12):3488-3491 (1998). In this method, nucleic acid targets are captured with magnetic beads containing specific capture primers. The beads with captured targets are washed and pelleted before adding amplification reagents which contains amplification primers, dNTP, NTP, 2500 U of reverse transcriptase and 2500 U of T7 RNA polymerase. A 100 µl TMA reaction mixture is placed in a tube, 200 µl oil reagent is added and amplification is accomplished by incubation at 42° C. in a waterbath for one hour.

NASBA is a transcription-based amplification method which amplifies RNA from either an RNA or DNA target. NASBA is a method used for the continuous amplification of nucleic acids in a single mixture at one temperature. For example, for RNA amplification, avian myeloblastosis virus (AMV) reverse transcriptase, RNase H and T7 RNA polymerase are used. This method can be performed as according to Heim, et al., Nucleic Acids Res., 26(9):2250-2251 (1998). Briefly, an NASBA reaction mixture contains two specific primers, dNTP, NTP, 6.4 U of AMV reverse transcriptase, 0.08 U of *Escherichia coli* Rnase H, and 32 U of T7 RNA polymerase. The amplification is carried out for 120 min at 41° C. in a total volume of 20 µl.

In a related method, self-sustained sequence-replication (3SR) reaction, isothermal amplification of target DNA or RNA sequences in vitro using three enzymatic activities: reverse transcriptase, DNA-dependent RNA polymerase and *Escherichia coli* ribonuclease H. This method may be modified from a 3-enzyme system to a 2-enzyme system by using human immunodeficiency virus (HIV)-1 reverse transcriptase instead of avian myeloblastosis virus (AMV) reverse transcriptase to allow amplification with T7 RNA polymerase but without *E. coli* ribonuclease H. In the 2-enzyme 3SR, the amplified RNA is obtained in a purer form compared with the 3-enzyme 3SR (Gebinoga & Oehlenschlager Eur J Biochem, 235:256-261, 1996).

SDA is an isothermal nucleic acid amplification method. A primer containing a restriction site is annealed to the template. Amplification primers are then annealed to 5' adjacent sequences (forming a nick) and amplification is started at a fixed temperature. Newly synthesized DNA strands are nicked by a restriction enzyme and the polymerase amplification begins again, displacing the newly synthesized strands. SDA can be performed as according to Walker, et al., PNAS, 89:392-6 (1992). Briefly, an SDA reaction mixture contains four SDA primers, dGTP, dCTP, TTP, dATP, 150 U of Hinc II, and 5 U of exonuclease-deficient of the large fragment of *E. coli* DNA polymerase I (exo-Klenow polymerase). The sample mixture is heated 95° C. for 4 minutes to denature target DNA prior to addition of the enzymes. After addition of the two enzymes, amplification is carried out for 120 min. at 37° C. in a total volume of 50 µl. Then, the reaction is terminated by heating for 2 min. at 95° C.

The Q-beta replication system uses RNA as a template. Q-beta replicase synthesizes the single-stranded RNA genome of the coliphage Qβ. Cleaving the RNA and ligating in a nucleic acid of interest allows the replication of that sequence when the RNA is replicated by Q-beta replicase (Kramer & Lizardi Trends Biotechnol. 1991 9(2):53-8, 1991).

A variety of amplification enzymes are well known in the art and include, for example, DNA polymerase, RNA polymerase, reverse transcriptase, Q-beta replicase, thermostable DNA and RNA polymerases. Because these and other amplification reactions are catalyzed by enzymes, in a single step assay the nucleic acid releasing reagents and the detection reagents should not be potential inhibitors of amplification enzymes if the ultimate detection is to be amplification based. Amplification methods suitable for use with the present methods include, for example, strand displacement amplification, rolling circle amplification, primer extension preamplification, or degenerate oligonucleotide PCR (DOP). These methods of amplification are well known in the art and each described briefly below.

In suitable embodiments, PCR is used to amplify a target or marker sequence of interest. The skilled artisan is capable of designing and preparing primers that are appropriate for amplifying a target or marker sequence. The length of the amplification primers depends on several factors including the nucleotide sequence identity and the temperature at which these nucleic acids are hybridized or used during in vitro nucleic acid amplification. The considerations necessary to determine a preferred length for an amplification primer of a particular sequence identity are well-known to a person of ordinary skill. For example, the length of a short nucleic acid or oligonucleotide can relate to its hybridization specificity or selectivity.

For analyzing mutations and other variant nucleic acids, it may be appropriate to use oligonucleotides specific for alternative alleles. Such oligonucleotides which detect single nucleotide variations in target sequences may be referred to by such terms as "allele-specific probes", or "allele-specific primers". The design and use of allele-specific probes for analyzing polymorphisms is described in, e.g., Mutation Detection A Practical Approach, ed. Cotton et al. Oxford University Press, 1998; Saiki et al., Nature, 324:163-166 (1986); Dattagupta, EP235,726; and Saiki, WO 89/11548. In one embodiment, a probe or primer may be designed to hybridize to a segment of target DNA such that the SNP aligns with either the 5' most end or the 3' most end of the probe or primer.

In some embodiments, the amplification may include a labeled primer, thereby allowing detection of the amplification product of that primer. In particular embodiments, the amplification may include a multiplicity of labeled primers; typically, such primers are distinguishably labeled, allowing the simultaneous detection of multiple amplification products.

In one type of PCR-based assay, an allele-specific primer hybridizes to a region on a target nucleic acid molecule that overlaps a SNP position and only primes amplification of an allelic form to which the primer exhibits perfect complementarity (Gibbs, 1989, Nucleic Acid Res., 17:2427-2448). Typically, the primer's 3'-most nucleotide is aligned with and complementary to the SNP position of the target nucleic acid molecule. This primer is used in conjunction with a second primer that hybridizes at a distal site. Amplification proceeds from the two primers, producing a detectable product that indicates which allelic form is present in the test sample. A control is usually performed with a second pair of primers, one of which shows a single base mismatch at the polymorphic site and the other of which exhibits perfect complementarity to a distal site. The single-base mismatch prevents amplification or substantially reduces amplification efficiency, so that either no detectable product is formed or it is formed in lower amounts or at a slower pace. The method generally works most effectively when the mismatch is at the 3'-most position of the oligonucleotide (i.e., the 3'-most position of the oligonucleotide aligns with the target mutation position) because this position is most destabilizing to elongation from the primer (see, e.g., WO 93/22456).

In a specific embodiment, a primer contains a sequence substantially complementary to a segment of a target mutation-containing nucleic acid molecule except that the primer has a mismatched nucleotide in one of the three nucleotide positions at the 3'-most end of the primer, such that the mismatched nucleotide does not base pair with a particular allele at the mutation site. In one embodiment, the mismatched nucleotide in the primer is the second from the last nucleotide at the 3'-most position of the primer. In another embodiment, the mismatched nucleotide in the primer is the last nucleotide at the 3'-most position of the primer.

In one embodiment, primer or probe is labeled with a fluorogenic reporter dye that emits a detectable signal. While a suitable reporter dye is a fluorescent dye, any reporter dye that can be attached to a detection reagent such as an oligonucleotide probe or primer is suitable for use in the invention. Such dyes include, but are not limited to, Acridine, AMCA, BODIPY, Cascade Blue, Cy2, Cy3, Cy5, Cy7, Dabcyl, Edans, Eosin, Erythrosin, Fluorescein, 6-Fam, Tet, Joe, Hex, Oregon Green, Rhodamine, Rhodol Green, Tamra, Rox, and Texas Red.

The present invention also contemplates reagents that do not contain (or that are complementary to) a mutated nucleotide sequence identified herein but that are used to assay one or more of the mutations disclosed herein. For example, primers that flank, but do not hybridize directly to a target position provided herein are useful in primer extension reactions in which the primers hybridize to a region adjacent to the target position (i.e., within one or more nucleotides from the target mutation site). During the primer extension reaction, a primer is typically not able to extend past a target mutation site if a particular nucleotide (allele) is present at that target site, and the primer extension product can readily be detected in order to determine which allele (i.e., wildtype or mutant) is present. For example, particular ddNTPs are typically used in the primer extension reaction to terminate primer extension once a ddNTP is incorporated into the extension product. Thus, reagents that bind to a nucleic acid molecule in a region adjacent to a mutation site, even though the bound sequences do not necessarily include the mutation site itself, are also encompassed by the present invention.

Detection of Variant Sequences.

Variant nucleic acids may be amplified prior to detection or may be detected directly during an amplification step (i.e., "real-time" methods). In some embodiments, the target sequence is amplified and the resulting amplicon is detected by electrophoresis. In some embodiments, the specific mutation or variant is detected by sequencing the amplified nucleic acid. In some embodiments, the target sequence is amplified using a labeled primer such that the resulting amplicon is detectably labeled. In some embodiments, the primer is fluorescently labeled.

In one embodiment, detection of a variant nucleic acid is performed using the TaqMan® assay, which is also known as the 5' nuclease assay (U.S. Pat. Nos. 5,210,015 and 5,538,848) or Molecular Beacon probe (U.S. Pat. Nos. 5,118,801 and 5,312,728), or other stemless or linear beacon probe (Livak et al., 1995, PCR Method Appl., 4:357-362; Tyagi et al, 1996, Nature Biotechnology, 14:303-308; Nazarenko et al., 1997, Nucl. Acids Res., 25:2516-2521; U.S. Pat. Nos. 5,866,336 and 6,117,635). The TaqMan® assay detects the accumulation of a specific amplified product during PCR. The TaqMan® assay utilizes an oligonucleotide probe labeled with a fluorescent reporter dye and a quencher dye. The reporter dye is excited by irradiation at an appropriate wavelength, it transfers energy to the quencher dye in the same probe via a process called fluorescence resonance energy transfer (FRET). When attached to the probe, the excited reporter dye does not emit a signal. The proximity of the quencher dye to the reporter dye in the intact probe maintains a reduced fluorescence for the reporter. The reporter dye and quencher dye may be at the 5' most and the 3' most ends, respectively or vice versa. Alternatively, the reporter dye may be at the 5' or 3' most end while the quencher dye is attached to an internal nucleotide, or vice versa. In yet another embodiment, both the reporter and the quencher may be attached to internal nucleotides at a distance from each other such that fluorescence of the reporter is reduced.

During PCR, the 5' nuclease activity of DNA polymerase cleaves the probe, thereby separating the reporter dye and the quencher dye and resulting in increased fluorescence of the reporter. Accumulation of PCR product is detected directly by monitoring the increase in fluorescence of the reporter dye. The DNA polymerase cleaves the probe between the reporter dye and the quencher dye only if the probe hybridizes to the target SNP-containing template which is amplified during PCR, and the probe is designed to hybridize to the target SNP site only if a particular SNP allele is present.

TaqMan® primer and probe sequences can readily be determined using the variant and associated nucleic acid sequence information provided herein. A number of computer programs, such as Primer Express (Applied Biosystems, Foster City, Calif.), can be used to rapidly obtain optimal primer/probe sets. It will be apparent to one of skill in the art that such primers and probes for detecting the variants of the present invention are useful in diagnostic assays for neurodevelopmental disorders and related pathologies, and can be readily incorporated into a kit format. The present invention also includes modifications of the TaqMan® assay well known in the art such as the use of Molecular Beacon probes (U.S. Pat. Nos. 5,118,801 and 5,312,728) and other variant formats (U.S. Pat. Nos. 5,866, 336 and 6,117,635).

In an illustrative embodiment, real time PCR is performed using TaqMan® probes in combination with a suitable amplification/analyzer such as the ABI Prism® 7900HT Sequence Detection System. The ABI PRISM® 7900HT Sequence Detection System is a high-throughput real-time PCR system that detects and quantitates nucleic acid sequences. Briefly, TaqMan® probes specific for the amplified target or marker sequence are included in the PCR amplification reaction. These probes contain a reporter dye at the 5' end and a quencher dye at the 3' end. Probes hybridizing to different target or marker sequences are conjugated with a different fluorescent reporter dye. During PCR, the fluorescently labeled probes bind specifically to their respective target or marker sequences; the 5' nuclease activity of Taq polymerase cleaves the reporter dye from the probe and a fluorescent signal is generated. The increase in fluorescence signal is detected only if the target or marker sequence is complementary to the probe and is amplified during PCR. A mismatch between probe and target greatly reduces the efficiency of probe hybridization and cleavage. The ABI Prism 7700HT or 7900HT Sequence detection System measures the increase in fluorescence during PCR thermal cycling, providing "real time" detection of PCR product accumulation. Real time detection on the ABI Prism 7900HT or 7900HT Sequence Detector monitors fluorescence and calculates Rn during each PCR cycle. The threshold cycle, or Ct value, is the cycle at which fluorescence intersects the threshold value. The threshold value is determined by the sequence detection system software or manually.

Other methods of probe hybridization detected in real time can be used for detecting amplification a target or marker sequence flanking a tandem repeat region. For example, the commercially available MGB Eclipse™ probes (Epoch Biosciences), which do not rely on a probe degradation can be used. MGB Eclipse™ probes work by a hybridization-triggered fluorescence mechanism. MGB Eclipse™ probes have the Eclipse™ Dark Quencher and the MGB positioned at the 5'-end of the probe. The fluorophore is located on the 3'-end of the probe. When the probe is in solution and not hybridized, the three dimensional conformation brings the quencher into close proximity of the fluorophore, and the fluorescence is quenched. However, when the probe anneals to a target or marker sequence, the probe is unfolded, the quencher is moved from the fluorophore, and the resultant fluorescence can be detected.

Oligonucleotide probes can be designed which are between about 10 and about 100 nucleotides in length and hybridize to the amplified region. Oligonucleotides probes are preferably 12 to 70 nucleotides; more preferably 15-60 nucleotides in length; and most preferably 15-25 nucleotides in length. The probe may be labeled. Amplified fragments may be detected using standard gel electrophoresis methods. For example, in preferred embodiments, amplified fractions are separated on an agarose gel and stained with ethidium bromide by methods known in the art to detect amplified fragments.

Another suitable detection methodology involves the design and use of bipartite primer/probe combinations such as Scorpion™ probes. These probes perform sequence-specific priming and PCR product detection is achieved using a single molecule. Scorpion™ probes comprise a 3' primer with a 5' extended probe tail comprising a hairpin structure which possesses a fluorophore/quencher pair. The probe tail is "protected" from replication in the 5' to 3' direction by the inclusion of hexethlyene glycol (HEG) which blocks the polymerase from replicating the probe. The fluorophore is attached to the 5' end and is quenched by a moiety coupled to the 3' end. After extension of the Scorpion™ primer, the specific probe sequence is able to bind to its complement within the extended amplicon thus opening up the hairpin loop. This prevents the fluorescence from being quenched and a signal is observed. A specific target is amplified by the reverse primer and the primer portion of the Scorpion™, resulting in an extension product. A fluorescent signal is generated due to the separation of the fluorophore from the quencher resulting from the binding of the probe element of the Scorpion™ to the extension product. Such probes are described in Whitcombe et al., Nature Biotech 17: 804-807 (1999).

Isolation of MPL Proteins

MPL proteins with and without insertion/truncation mutation may be recovered from biological sample from an individual, culture medium or from host cell lysates. If membrane-bound, it can be released from the membrane using a suitable detergent solution (e.g., Triton-X 100) or by enzymatic cleavage. Cells employed in the expression of MPL protein can be disrupted by various physical or chemical means, such as freeze-thaw cycling, sonication, mechanical disruption, or cell lysing agents.

It may be desired to purify MPL protein from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the BCR-ABL. Various methods of protein purification may be employed and such methods are known in the art and described for example in Deutscher, Methods in Enzymology (1990), 182:83-89; Scopes, Protein Purification: Principles and Practice, Springer-Verlag, New York (1982). The purification step(s) selected will depend, for example, on the nature of the production process, source of MPL used and the particular MPL produced.

Detection of MPL Proteins

Several methods for detection of proteins are well known in the art. Detection of the proteins could be by resolution of the proteins by SDS polyacrylamide gel electrophoresis (SDS PAGE), followed by staining the proteins with suitable stain for example, Coomassie Blue. The MPL proteins with and without a mutation can be differentiated from each other and also from other proteins by Western blot analysis using mutation-specific antibodies. Methods of Western blot are well known in the art and described for example in W. Burnette W. N. Anal. Biochem. 1981; 112 (2): 195-203.

Alternatively, flow cytometry may be applied to detect the mutant and wildtype MPL protein. Antibodies specific for either the mutant or wildtype protein can be coupled to beads and can be used in the flow cytometry analysis.

In some embodiments, protein microarrays may be applied to identify the various MPL protein variants. Methods of protein arrays are well known in the art. In one example, antibodies specific for each protein may be immobilized on the solid surface such as glass or nylon membrane. The proteins can then be immobilized on the solid surface through the binding of the specific antibodies. Antibodies may be applied that bind specifically to a second epitope (e.g., an epitope common to the mutant and wildtype) of the MPL proteins. The first antibody/protein/second antibody complex can then be detected using a detectably labeled secondary antibody. The detectable label can be detected as discussed for polynucleotides.

Antibody Production and Screening

Various procedures known in the art may be used for the production of antibodies to epitopes of the MPL protein that may be used to distinguish among the protein variants. Such antibodies include but are not limited to polyclonal, monoclonal, chimeric, single chain, Fab fragments and fragments produced by a Fab expression library.

Antibodies may be radioactively labeled allowing one to follow their location and distribution in the body after injection. Radioactivity tagged antibodies may be used as a non-invasive diagnostic tool for imaging de novo cells of tumors and metastases.

Immunotoxins may also be designed which target cytotoxic agents to specific sites in the body. For example, high affinity MPL-specific monoclonal antibodies may be covalently complexed to bacterial or plant toxins, such as diphtheria toxin, abrin or ricin. A general method of preparation of antibody/hybrid molecules may involve use of thiol-crosslinking reagents such as SPDP, which attack the primary amino groups on the antibody and by disulfide exchange, attach the toxin to the antibody. The hybrid antibodies may be used to specifically eliminate mutant MPL protein-expressing cells.

For the production of antibodies, various host animals may be immunized by injection with the full length or fragment of MPL proteins including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum*.

Monoclonal antibodies to MPL proteins may be prepared by using any technique which provides for the production of antibody molecules by continuous cell lines in culture. These include but are not limited to the hybridoma technique originally described by Kohler and Milstein, (Nature (1975), 256:495-497), the human B-cell hybridoma technique (Kosbor et al., Immunology Today (1983), 4:72; Cote et al. Proc.

Natl. Acad. Sci. (1983), 80:2026-2030) and the EBV-hybridoma technique (Cole et al., Monoclonal Antibodies and Cancer Therapy (1985), Alan R. Liss, Inc., pp. 77-96). In addition, techniques developed for the production of "chimeric antibodies" (Morrison et al., Proc. Natl. Acad. Sci. USA (1984), 81:6851-6855; Neuberger et al., Nature (1984), 312:604-608; Takeda et al., Nature (1985), 314:452-454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce MPL protein-specific single chain antibodies.

Antibody fragments may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., Science. 1989; 246: 1275-1281) to allow rapid and easy identification of monoclonal Fab fragments with the desired specificity.

Kits

The present inventions also contemplate diagnostic systems in kit form. A diagnostic system of the present inventions may include a kit which contains, in an amount sufficient for at least one assay, any of the hybridization assay probes, amplification primers, and/or antibodies against MPL wild type and mutant proteins in a packaging material. Typically, the kits will also include instructions recorded in a tangible form (e.g., contained on paper or an electronic medium) for using the packaged probes, primers, and/or antibodies in a detection assay for determining the presence or amount of variant mRNA or protein in a test sample.

The various components of the diagnostic systems may be provided in a variety of forms. For example, the required enzymes, the nucleotide triphosphates, the probes, primers, and/or antibodies may be provided as a lyophilized reagent. These lyophilized reagents may be pre-mixed before lyophilization so that when reconstituted they form a complete mixture with the proper ratio of each of the components ready for use in the assay. In addition, the diagnostic systems of the present inventions may contain a reconstitution reagent for reconstituting the lyophilized reagents of the kit. In preferred kits, the enzymes, nucleotide triphosphates and required cofactors for the enzymes are provided as a single lyophilized reagent that, when reconstituted, forms a proper reagent for use in the present amplification methods.

Some preferred kits may further contain a solid support for anchoring the nucleic acid of interest on the solid support. The target nucleic acid may be anchored to the solid support directly or indirectly through a capture probe anchored to the solid support and capable of hybridizing to the nucleic acid of interest. Examples of such solid support include but are not limited to beads, microparticles (for example, gold and other nano particles), microarray, microwells, multiwell plates. The solid surfaces may comprise a first member of a binding pair and the capture probe or the target nucleic acid may comprise a second member of the binding pair. Binding of the binding pair members will anchor the capture probe or the target nucleic acid to the solid surface. Examples of such binding pairs include but are not limited to biotin/streptavidin, hormone/receptor, ligand/receptor, antigen/antibody.

EXAMPLES

Example 1: JAK2 Mutation Analysis

A total of 2790 EDTA peripheral blood samples from patients with suspected MPNs were tested for JAK2 and MPL mutations. Whole blood samples were shipped at room temperature and plasma was separated for RNA extraction within 24 hours. JAK2 mutation analysis was performed to detect V617F and exons 12, 13, 14, and partial exon 15 mutations. After the initial screen for JAK2 mutations, MPL exon 10-11 mutation analysis was performed on JAK2 mutation-negative samples.

Total nucleic acids were isolated from EDTA plasma samples by EasyMag® extraction kit (BioMerieux Inc., Durham, N.C.) following the manufacturer's instructions. Primer pair was designed to encompass the JAK2 exon 12 and V617F point mutation. The primer set with 18 bp M13 tag used to amplify 491-bp JAK2 product was: 5'-tgt aaa acg acg gcc agt CTA AAT GCT GTC CCC CAA AG-3' (SEQ ID NO: 3) (forward) and 5'-cag gaa aca gct atg acc CCA TGC CAA CTG TTT AGC AA-3' (SEQ ID NO: 4) (reverse). The RT-PCR was performed using Superscript® III one step RT-PCR systems with Platinum® Taq (Invitrogen, Carlsbad, Calif.) with the following thermocycler conditions: 55° C. for 30 min and 94° C. for 2 min, followed by 40 cycles of 94° C. for 15 second, 60° C. for 30 second, and 68° C. for 1 min and a final extension step of 68° C. for 7 min. The PCR product was then purified and sequenced in both forward and reverse directions using ABI PRISM® 3730XL Genetic Analyzer (Applied Biosystems, Foster City, Calif.). Sequencing data are base-called by sequencing analysis software and assembled and analyzed by SeqScape® software using GenBank accession number NM 004972 as reference.

JAK2 mutations were detected in 548 of the 2790 patient samples (19.64%, Table 1). The V617F mutation was the most prevalent mutation detected (529/2790, 18.96%), followed by exon 12 small insertion/deletion (12/2790, 0.43%). The exon 12 mutation patterns were published in our previous study. (Ma et al., 2009) The exon 13-15 point mutations and the Dexon 14 splice mutation account for the balance of the positive results (7/2790, 0.25%).

TABLE 1

JAK2 Mutations Found in Patients with Suspected MPNs

| Mutation | # of Positives | Mutation Type | % of Positives |
| --- | --- | --- | --- |
| V617F | 529 | V617F | 18.96% |
| Exon 12 | 12 | Small indel | 0.43% |
| Exon 13 | 2 | R564L, G571S | 0.07% |
| Exon 14 splice | 2 | Exon 14 del | 0.07% |
| Exon 14 | 2 | H606Q, C618R | 0.07% |
| Exon 15 | 1 | L624P | 0.04% |
| Total | 548 | | 19.64% |

Example 2: MPL Mutation Analysis

The remaining (JAK2 mutation-negative) RNA samples (n=2242) were tested for MPL exon 10-11 mutations. Total nucleic acids were extracted from plasma using EasyMag extraction kit (BioMerieux) as above. The primer pair was designed to encompass the MPL gene located in chromosome 1p34, exon 10 &11. The primer sequences with 18-bp M13 tag was: tgt aaa acg acg gcc agtGCG ATC TCG CTA CCG TTT AC (SEQ ID NO: 5) (forward) and cag gaa aca gct atg acc GAG GAC TTG GGG AGG ATT TC (SEQ ID NO: 6) (reverse). A 366 bp PCR product was amplified from patient's RNA using Superscript III one step RT-PCR (Invitrogen). The PCR product was then purified and sequenced in both forward and reverse directions using the ABI PRISM 3730XL Genetic Analyzer. Sequencing data are base-called by sequencing analysis software and assembled and analyzed by SeqScape software using GenBank accession number NM 005373 (SEQ ID NO: 1) as reference.

MPL mutations were detected in 68 of the 2242 (3.03%) samples (Table 2). Most of the MPL mutations were in exon 10 (64/68, 94.1%); the exon 11 mutations were less common (4/68, 5.9%). W515L (tgg>ttg) was the most dominant mutation (46/68, 67.7%); 43 patients were heterozygous and 3 patients were homozygous W515L (FIG. 1). Thus, similar to homozygous JAK2 V617F mutation, the W515 normal allele can be lost completely. Six other W515 variants were detected (11/68, 16.2%), which include one, two, or all three nucleotide changes in codon 515 (Table 2). Thus, MPL W515 mutations are the most prevalent (57/68, 83.82%). Mutation in the other codons (V501, S505, V507, R514, and A519 in exon 10 and D545 in exon 11) together account for 11.8% (8/68). Two patients were positive for more than one MPL mutant allele: one patient carries W515L and exon 11 G540S and the other patient carries both S505N and V501 L mutant alleles. The S505N was reported previously as a heritable predisposition allele in familial essential thrombocythemia. (Ding et al. Blood, 103: 4198-4220, 2004).

Figure 2:
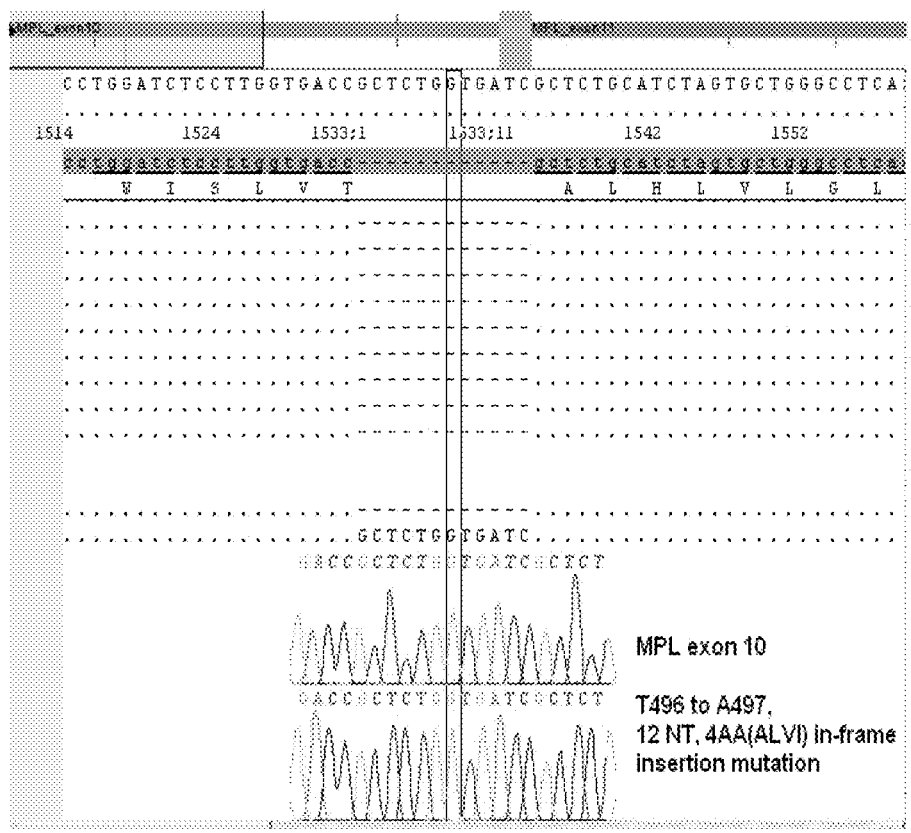
FIG. 2. is a representative sequence tracing showing a 12-nucleotide insertion at C1553_G1534 resulting in the addition of ALVI amino acids.
Figure 3:
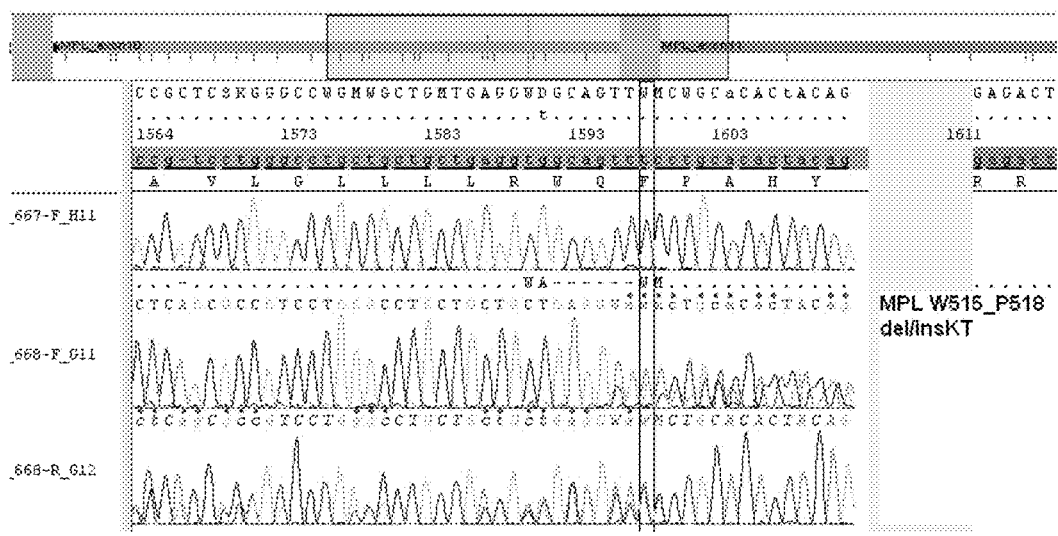
FIG. 3 is a representative sequence tracing showing detection of an insertion/deletion MPL mutation in exon 10.
Figure 4:
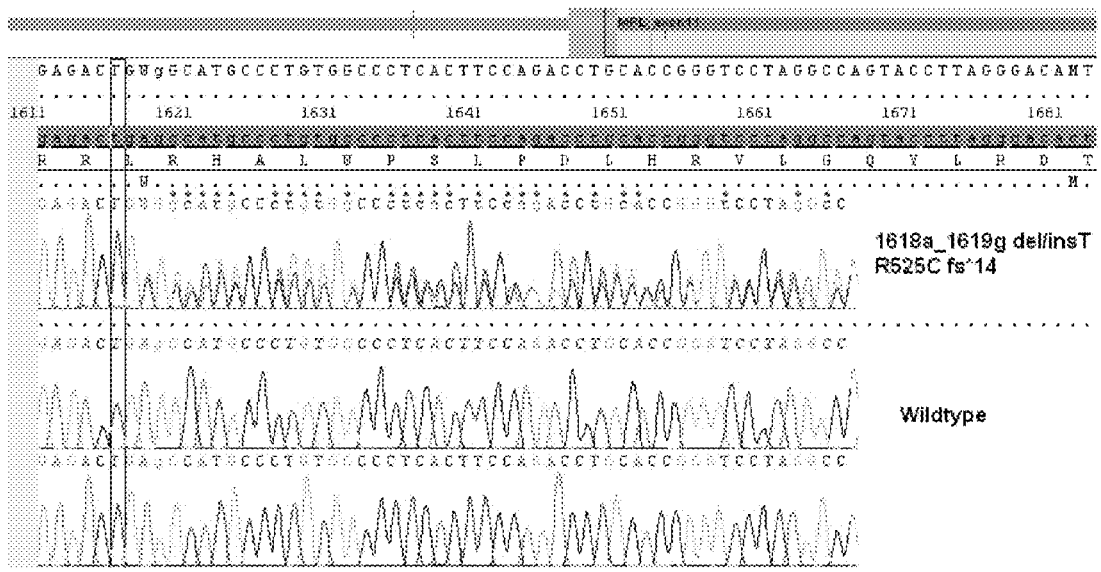
FIG. 4 is a representative sequence tracing showing detection of an insertion/deletion MPL mutation in exon 11.

Whereas, most published MPL mutations are point mutations, the present study identified three MPL insertion/deletion mutations in exons 10 and 11 (3/68, 4.4%): 1) The exon 10 gct ctg gtg atc (SEQ ID NO: 7) 12-nucleotide insertion at C1533_G1534 of SEQ ID NO: 1 causes a 4-amino acid insertion (ALVI) at position T496_A497 of SEQ ID NO: 2 (FIG. 2); this homozygous in-frame insertion was detected in one patient with confirmed diagnosis of idiopathic myelofibrosis (IMF). 2) The heterozygous T1588_31599 del/ins 6 mutation in-frame mutation in exon 10 (resulting in the W515_P518 del/insKT mutation in the MPL protein) was detected in a patient with unspecified MPN (FIG. 3). 3) A MPL exon 11 small indel 1618_1619 ag del/ins T was detected in an unspecified MPN patient (FIG. 4). This MPL small indel causes frameshift and truncated MPL protein R525C fs*14. We expect that all MPL insertion/deletion mutants behave similarly to the W515 mutant; the mutations induce the myeloid proliferative advantage leading to MPNs. The MPL mutation profile from this study indicated that more than 20% of MPL mutations would have been missed if only W515L and W515K were analyzed, as would be the case using allele-specific PCR analysis.

TABLE 2

MPL Mutation Profile in JAK2 Mutation-negative MPNs

| Codon # | Nucleotide Change | Amino Acid Change | # of Positives | % of Positives |
|---|---|---|---|---|
| W515 | tgg > ttg | W515[W, L] | 43 | 67.19% |
| W515 | tgg > ttg | W515L, homo | 3 | 4.69% |
| W515 | tgg > agg | W515[W, R] | 3 | 4.69% |
| W515 | tgg > agg | W515[R, *, K, W] | 3 | 4.69% |
| W515 | tgg > tcg | W515[W, S] | 2 | 3.13% |
| W515 | tgg > aaa | W515[K, R, * W] | 1 | 1.56% |

TABLE 2-continued

MPL Mutation Profile in JAK2 Mutation-negative MPNs

| Codon # | Nucleotide Change | Amino Acid Change | # of Positives | % of Positives |
|---|---|---|---|---|
| W515 | tgg > gcg | W515[A, G, S, W] | 1 | 1.56% |
| W515 and G540 | tgg > ttg ggc > agc | W515[W, L] + G540[G, S] | 1 | 1.56% |
| S505 | agc > acc | S505[S, N] | 2 | 3.13% |
| S505 and V501 | agc > acc gtg > ctg | S505N + V501L | 1 | 1.56% |
| V507 | gtc > atc | V507[V, I] | 1 | 1.56% |
| R514 | agg > aag | R514[R, K] | 1 | 1.56% |
| A519 | gca > gta | A519[A, V] | 1 | 1.56% |
| D545 | gac > ggc | D545[D, G] | 1 | 1.56% |
| D545 | gac > aac | D545[D, N] | 1 | 1.56% |
| W515_P518 | tgg cag ttt cct del/ins aaa act | W515_P518 del/ins KT | 1 | 1.56% |
| T496_A497 | gct ctg gtg atc ins | T496_A497 ALVI ins, homo | 1 | 1.56% |
| R525 | 1618_1619ag del/ins T | p. R525C fs*14 | 1 | 1.56% |
| Total | | | 68 | |

In addition to the insertion/deletion mutations described above, this study identified additional point mutations (SNPs) and amino acid substitutions including D545G, D545N, R537Q (cgg>cag; SNP rs3820551), T496 (acc>act; silent polymorphism), L543 (ctt>ctc; silent polymorphism), and D534 (gac>gat; silent polymorphism).

Unless otherwise defined, all technical and scientific terms used herein have the same meaning as commonly understood by one of ordinary skill in the art to which this invention belongs. All nucleotide sequences provided herein are presented in the 5' to 3' direction.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

What is claimed is:

1. A method of detecting a T1588 T1599 del/ins6 mutation in the myeloproliferative leukemia (MPL) gene in an individual, comprising:
   (a) contacting a sample containing a MPL nucleic acid from an individual suspected of having a mutation in the MPL gene with a detectably labeled nucleic acid probe that hybridizes to a mutant MPL nucleic acid comprising the T1588 T1599 del/ins6 mutation but not to a wild type MPL nucleic acid, wherein the nucleic acid probe comprises the sequence set forth in SEQ ID NO:10; and
   (b) detecting a hybrid formed between the detectably labeled nucleic acid probe and the mutant MPL nucleic acid.

2. The method of claim 1, wherein said sample is selected from the group consisting of blood, serum, and plasma.

3. The method of claim 1, wherein said individual does not have a pathologic mutation in the JAK2 gene.

4. The method of claim 1, wherein said individual does not have a mutation in the JAK2 gene encoding V617F mutation.

5. The method of claim 1, wherein the individual is suspected of having a myeloproliferative disease.

6. The method of claim 5, wherein said myeloproliferative disease is selected from the group consisting of polycythemia vera (PV), essential thrombocythemia (ET), and idiopathic myelofibrosis (IMF).

7. The method of claim 1, wherein said MPL nucleic acid from the individual is mRNA or genomic DNA.

8. The method of claim 7, further comprising reverse transcription of MPL mRNA to cDNA.

9. The method of claim 1, further comprising nucleic acid amplification.

10. The method of claim 9, wherein the nucleic acid amplification is allele specific amplification.

11. The method of claim 1, wherein the method comprises a 5' nuclease assay.

* * * * *

SEQUENCE LISTING

<160> NUMBER OF SEQ ID NOS: 38

<210> SEQ ID NO 1
<211> LENGTH: 3645
<212> TYPE: DNA
<213> ORGANISM: Homo sapiens

<400> SEQUENCE: 1

| | | | | | |
|---|---|---|---|---|---|
| cctgaaggga | ggatgggcta | aggcaggcac | acagtggcgg | agaagatgcc | ctcctgggcc | 60 |
| ctcttcatgg | tcacctcctg | cctcctcctg | gcccctcaaa | acctggccca | agtcagcagc | 120 |
| caagatgtct | ccttgctggc | atcagactca | gagccctga | agtgtttctc | ccgaacattt | 180 |
| gaggacctca | cttgcttctg | ggatgaggaa | gaggcagcgc | ccagtgggac | ataccagctg | 240 |
| ctgtatgcct | acccgcggga | gaagcccgt | gcttgccccc | tgagttccca | gagcatgccc | 300 |
| cactttggaa | cccgatacgt | gtgccagttt | ccagaccagg | aggaagtgcg | tctcttcttt | 360 |
| ccgctgcacc | tctgggtgaa | gaatgtgttc | ctaaaccaga | ctcggactca | gcgagtcctc | 420 |
| tttgtggaca | gtgtaggcct | gccggctccc | cccagtatca | tcaaggccat | gggtgggagc | 480 |
| cagccagggg | aacttcagat | cagctgggag | gagccagctc | cagaaatcag | tgatttcctg | 540 |
| aggtacgaac | tccgctatgg | ccccagagat | cccaagaact | ccactggtcc | cacggtcata | 600 |
| cagctgattg | ccacagaaac | ctgctgccct | gctctgcaga | ggcctcactc | agcctctgct | 660 |
| ctggaccagt | ctccatgtgc | tcagcccaca | atgccctggc | aagatggacc | aaagcagacc | 720 |
| tccccaagta | gagaagcttc | agctctgaca | gcagagggtg | gaagctgcct | catctcagga | 780 |
| ctccagcctg | gcaactccta | ctggctgcag | ctgcgcagcg | aacctgatgg | gatctccctc | 840 |
| ggtggctcct | ggggatcctg | gtccctcctt | gtgactgtgg | acctgcctgg | agatgcagtg | 900 |
| gcacttggac | tgcaatgctt | taccttggac | ctgaagaatg | ttacctgtca | atggcagcaa | 960 |
| caggaccatg | ctagctccca | aggcttcttc | taccacagca | gggcacggtg | ctgccccaga | 1020 |
| gacaggtacc | ccatctggga | gaactgcgaa | gaggaagaga | aaacaaatcc | aggactacag | 1080 |
| accccacagt | tctctcgctg | ccacttcaag | tcacgaaatg | acagcattat | tcacatcctt | 1140 |
| gtggaggtga | ccacagcccc | gggtactgtt | cacagctacc | tgggctcccc | tttctggaatc | 1200 |
| caccaggctg | tgcgcctccc | caccccaaac | ttgcactgga | gggagatctc | cagtgggcat | 1260 |
| ctggaattgg | agtggcagca | cccatcgtcc | tgggcagccc | aagagacctg | ttatcaactc | 1320 |
| cgatacacag | gagaaggcca | tcaggactgg | aaggtgctgg | agccgcctct | cggggcccga | 1380 |
| ggagggaccc | tggagctgcg | cccgcgatct | cgctaccgtt | tacagctgcg | cgccaggctc | 1440 |
| aacggcccca | cctaccaagg | tccctggagc | tcgtggtcgg | acccaactag | ggtgagacc | 1500 |
| gccaccgaga | ccgcctggat | ctccttggtg | accgctctgc | atctagtgct | gggcctcagc | 1560 |
| gccgtcctgg | gcctgctgct | gctgaggtgg | cagtttcctg | cacactacag | gagactgagg | 1620 |
| catgccctgt | ggccctcact | tccagacctg | caccgggtcc | taggccagta | ccttagggac | 1680 |
| actgcagccc | tgagcccgcc | caaggccaca | gtctcagata | cctgtgaaga | agtggaaccc | 1740 |
| agcctccttg | aaatcctccc | caagtcctca | gagaggactc | ctttgccct | gtgttcctcc | 1800 |
| caggcccaga | tggactaccg | aagattgcag | ccttcttgcc | tggggaccat | gcccctgtct | 1860 |
| gtgtgcccac | ccatggctga | gtcagggtcc | tgctgtacca | cccacattgc | caaccattcc | 1920 |
| tacctaccac | taagctattg | gcagcagcct | tgaggacagg | ctcctcactc | ccagttccct | 1980 |
| ggacagagct | aaactctcga | gacttctctg | tgaacttccc | tacccttaccc | ccacaacaca | 2040 |
| agcacccag | acctcacctc | catcccctc | tgtctgccct | cacaattagg | cttcattgca | 2100 |

```
ctgatcttac tctactgctg ctgacataaa accaggaccc tttctccaca ggcaggctca    2160
tttcactaag ctcctccttt actttctctc tcctctttga tgtcaaacgc cttgaaaaca    2220
agcctccact tccccacact tcccatttac tcttgagact acttcaatta gttcccctac    2280
tacactttgc tagtgaaact gcccaggcaa agtgcacctc aaatcttcta attccaagat    2340
ccaataggat ctcgttaatc atcagttcct ttgatctcgc tgtaagattt gtcaaggctg    2400
actactcact tctcctttaa attctttcct accttggtcc tgcctctttg agtatattag    2460
taggtttttt ttatttgttt gagacagggt ctcactctgt cacccaggct gcagtgcaat    2520
ggcgcgatct cagctcactg caacctccac ctccgggttc aagcgattct tgtgcctcgg    2580
cctccctagt agctgggatt acaggcgcac accaccacac acagctaatt ttttttttt    2640 tttttttttt tttttttag acggagcctt gctctgttgc cagactggag tgcagtggca    2700
cgatctcggc tcactgcaac ctctgcctcc cgggttcaag ccattctgcc tcagcctccc    2760
aagtagctgg gagtacaggc gtctgccacc atgcctaatt ttttctatt tttaggagag    2820 accggttttc accacgttgg ccaggatggt ctcgatatcc tgatctcgtg atccgcctgc    2880
ctctgcctcc caaagtgctg ggattacagg tgtgacccac tgcgcacagc ccagctaat    2940 tttcatattt ttagtagaga cagggttttg ccatgttgcc caggctggtc ttgaactcct    3000
aacctcgggt gatccaccca ccttggcctc ccaaagtgtt aggattacag gcatgagcca    3060
ctgcgcccgg ctgagtgtac tagtagttaa gagaataaac tagatctaga atcagagctg    3120
gattcaattc ctgtccttca catttactag ctgtgcaacc ttgggcacat aacttaatgt    3180 cttttgagcct tagttttttc atctgtaaaa cagggataat aacagcaccc catagagttg    3240
tgacgaggat tgagataatc taagtaaagc acagtcccta ggacatagta atgattcat    3300 atatccgaac tactgttata attattcctt cttactctcc tcttctagca tttcttccaa    3360
ttattacagt ccttcaagat tccatttctt aacagtctcc aatcccatct attctctgcc    3420
tttactatat gttgaccatt ccaaagttct tatctctagc tcagacatct actacagcac    3480
tgtgatgctt tatgcaacta actgtttaca tatctgtccc ctgctactag attgtgagct    3540
ccttgaggga aaggaacatg atttatttgt ccttttcccc cagcacctag agtagtgctt    3600
ggtgcatgat agtaggcctt caataaattt tttctaaatg aatga                    3645
```

<210> SEQ ID NO 2
<211> LENGTH: 635
<212> TYPE: PRT
<213> ORGANISM: Homo sapiens

<400> SEQUENCE: 2

```
Met Pro Ser Trp Ala Leu Phe Met Val Thr Ser Cys Leu Leu Leu Ala
1               5                   10                  15

Pro Gln Asn Leu Ala Gln Val Ser Ser Gln Asp Val Ser Leu Leu Ala
            20                  25                  30

Ser Asp Ser Glu Pro Leu Lys Cys Phe Ser Arg Thr Phe Glu Asp Leu
        35                  40                  45

Thr Cys Phe Trp Asp Glu Glu Ala Ala Pro Ser Gly Thr Tyr Gln
    50                  55                  60

Leu Leu Tyr Ala Tyr Pro Arg Glu Lys Pro Arg Ala Cys Pro Leu Ser
65                  70                  75                  80

Ser Gln Ser Met Pro His Phe Gly Thr Arg Tyr Val Cys Gln Phe Pro
                85                  90                  95
```

-continued

```
Asp Gln Glu Glu Val Arg Leu Phe Phe Pro Leu His Leu Trp Val Lys
            100                 105                 110

Asn Val Phe Leu Asn Gln Thr Arg Thr Gln Arg Val Leu Phe Val Asp
        115                 120                 125

Ser Val Gly Leu Pro Ala Pro Pro Ser Ile Ile Lys Ala Met Gly Gly
130                 135                 140

Ser Gln Pro Gly Glu Leu Gln Ile Ser Trp Glu Glu Pro Ala Pro Glu
145                 150                 155                 160

Ile Ser Asp Phe Leu Arg Tyr Glu Leu Arg Tyr Gly Pro Arg Asp Pro
                165                 170                 175

Lys Asn Ser Thr Gly Pro Thr Val Ile Gln Leu Ile Ala Thr Glu Thr
            180                 185                 190

Cys Cys Pro Ala Leu Gln Arg Pro His Ser Ala Ser Ala Leu Asp Gln
        195                 200                 205

Ser Pro Cys Ala Gln Pro Thr Met Pro Trp Gln Asp Gly Pro Lys Gln
210                 215                 220

Thr Ser Pro Ser Arg Glu Ala Ser Ala Leu Thr Ala Glu Gly Gly Ser
225                 230                 235                 240

Cys Leu Ile Ser Gly Leu Gln Pro Gly Asn Ser Tyr Trp Leu Gln Leu
                245                 250                 255

Arg Ser Glu Pro Asp Gly Ile Ser Leu Gly Gly Ser Trp Gly Ser Trp
            260                 265                 270

Ser Leu Pro Val Thr Val Asp Leu Pro Gly Asp Ala Val Ala Leu Gly
        275                 280                 285

Leu Gln Cys Phe Thr Leu Asp Leu Lys Asn Val Thr Cys Gln Trp Gln
290                 295                 300

Gln Gln Asp His Ala Ser Ser Gln Gly Phe Phe Tyr His Ser Arg Ala
305                 310                 315                 320

Arg Cys Cys Pro Arg Asp Arg Tyr Pro Ile Trp Glu Asn Cys Glu Glu
                325                 330                 335

Glu Glu Lys Thr Asn Pro Gly Leu Gln Thr Pro Gln Phe Ser Arg Cys
            340                 345                 350

His Phe Lys Ser Arg Asn Asp Ser Ile Ile His Ile Leu Val Glu Val
        355                 360                 365

Thr Thr Ala Pro Gly Thr Val His Ser Tyr Leu Gly Ser Pro Phe Trp
370                 375                 380

Ile His Gln Ala Val Arg Leu Pro Thr Pro Asn Leu His Trp Arg Glu
385                 390                 395                 400

Ile Ser Ser Gly His Leu Glu Leu Glu Trp Gln His Pro Ser Ser Trp
                405                 410                 415

Ala Ala Gln Glu Thr Cys Tyr Gln Leu Arg Tyr Thr Gly Glu Gly His
            420                 425                 430

Gln Asp Trp Lys Val Leu Glu Pro Pro Leu Gly Ala Arg Gly Gly Thr
        435                 440                 445

Leu Glu Leu Arg Pro Arg Ser Arg Tyr Arg Leu Gln Leu Arg Ala Arg
450                 455                 460

Leu Asn Gly Pro Thr Tyr Gln Gly Pro Trp Ser Ser Trp Ser Asp Pro
465                 470                 475                 480

Thr Arg Val Glu Thr Ala Thr Glu Thr Ala Trp Ile Ser Leu Val Thr
                485                 490                 495

Ala Leu His Leu Val Leu Gly Leu Ser Ala Val Leu Gly Leu Leu Leu
            500                 505                 510

Leu Arg Trp Gln Phe Pro Ala His Tyr Arg Arg Leu Arg His Ala Leu
```

```
                515                 520                 525
Trp Pro Ser Leu Pro Asp Leu His Arg Val Leu Gly Gln Tyr Leu Arg
    530                 535                 540

Asp Thr Ala Ala Leu Ser Pro Pro Lys Ala Thr Val Ser Asp Thr Cys
545                 550                 555                 560

Glu Glu Val Glu Pro Ser Leu Leu Glu Ile Leu Pro Lys Ser Ser Glu
                565                 570                 575

Arg Thr Pro Leu Pro Leu Cys Ser Ser Gln Ala Gln Met Asp Tyr Arg
            580                 585                 590

Arg Leu Gln Pro Ser Cys Leu Gly Thr Met Pro Leu Ser Val Cys Pro
        595                 600                 605

Pro Met Ala Glu Ser Gly Ser Cys Cys Thr Thr His Ile Ala Asn His
    610                 615                 620

Ser Tyr Leu Pro Leu Ser Tyr Trp Gln Gln Pro
625                 630                 635

<210> SEQ ID NO 3
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgtaaaacga cggccagtct aaatgctgtc ccccaaag                            38

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
caggaaacag ctatgacccc atgccaactg tttagcaa                            38

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgtaaaacga cggccagtgc gatctcgcta ccgtttac                            38

<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
caggaaacag ctatgaccga ggacttgggg aggatttc                            38

<210> SEQ ID NO 7
<211> LENGTH: 12
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 7
gctctggtga tc                                                          12

<210> SEQ ID NO 8
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tggcagtttc ct                                                          12

<210> SEQ ID NO 9
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9 aaaact                                                                  6

<210> SEQ ID NO 10
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ggaaaactgc                                                             10

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Leu Leu Arg Lys Thr Ala His
1               5

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ccgctctggt gatcgc                                                      16

<210> SEQ ID NO 13
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 13

Val Thr Ala Leu Val Ile Ala Leu
1               5

<210> SEQ ID NO 14
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gactgtgcat g                                                           11

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Cys Met Pro Cys Gly Pro His Phe Gln Thr Cys Thr Gly Ser
1               5                   10

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Leu Val Ile
1

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Trp Gln Phe Pro
1

<210> SEQ ID NO 18
<211> LENGTH: 52
<212> TYPE: DNA
<213> ORGANISM: Homo sapiens

<400> SEQUENCE: 18
cgtcctgggc ctgctgctgc tgaggtkgca gtttcctgcm cmctacagga ga              52

<210> SEQ ID NO 19
<211> LENGTH: 52
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 19
cgtcctgggc ctgctgctgc tgaggttgca gtttcctgcm cmctacagga ga            52

<210> SEQ ID NO 20
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cgtcctgggc ctgctgctgc tgaggtggca gtttcctgca cactacagga ga            52

<210> SEQ ID NO 21
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Val Leu Gly Leu Leu Leu Leu Arg Trp Gln Phe Pro Ala His Tyr
1               5                   10                  15
Arg Arg

<210> SEQ ID NO 22
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gaggttgcag t                                                         11

<210> SEQ ID NO 23
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gaggtggcag t                                                         11

<210> SEQ ID NO 24
<211> LENGTH: 57
<212> TYPE: DNA
<213> ORGANISM: Homo sapiens

<400> SEQUENCE: 24
cctggatctc cttggtgacc gctctggtga tcgctctgca tctagtgctg ggcctca       57

<210> SEQ ID NO 25
<211> LENGTH: 45
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 25
cctggatctc cttggtgacc gctctgcatc tagtgctggg cctca                    45

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Trp Ile Ser Leu Val Thr Ala Leu His Leu Val Leu Gly Leu
1               5                  10

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gaccgctctg gtgatcgctc t                                              21

<210> SEQ ID NO 28
<211> LENGTH: 56
<212> TYPE: DNA
<213> ORGANISM: Homo sapiens

<400> SEQUENCE: 28
ccgctcskgg gccwgmwgct gmtgaggwdg cagttwmcwg cacactacag gagact        56

<210> SEQ ID NO 29
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ccgctcskgg gccwgmwgct gmtgaggwtg cagttwmcwg cacactacag gagact        56

<210> SEQ ID NO 30
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ccgtcctggg cctgctgctg ctgaggtggc agtttcctgc acactacagg agact         55

<210> SEQ ID NO 31
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 31

Ala Val Leu Gly Leu Leu Leu Leu Arg Trp Gln Phe Pro Ala His Tyr
1               5                   10                  15

Arg Arg

<210> SEQ ID NO 32
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ccgtcctggg cctgctgctg ctgaggwawm ctgcacacta caggagact           49

<210> SEQ ID NO 33
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ctcagcgccg tcctgggcct gctgctgctg aggwawmctg cacactacag           50

<210> SEQ ID NO 34
<211> LENGTH: 73
<212> TYPE: DNA
<213> ORGANISM: Homo sapiens

<400> SEQUENCE: 34
gagactgwgg catgccctgt ggccctcact tccagacctg caccgggtcc taggccagta    60
ccttagggac amt                                                       73

<210> SEQ ID NO 35
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gagactgagg catgccctgt ggccctcact tccagacctg caccgggtcc taggccagta    60
ccttagggac act                                                       73

<210> SEQ ID NO 36
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Arg Leu Arg His Ala Leu Trp Pro Ser Leu Pro Asp Leu His Arg
1               5                   10                  15

Val Leu Gly Gln Tyr Leu Arg Asp Thr
            20                  25

```
<210> SEQ ID NO 37
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gagactgwgg catgccctgt ggccctcact tccagacctg caccgggtcc taggcc          56

<210> SEQ ID NO 38
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gagactgagg catgccctgt ggccctcact tccagacctg caccgggtcc taggcc          56
```